(12) United States Patent
Bringmann et al.

(10) Patent No.: US 8,173,673 B2
(45) Date of Patent: May 8, 2012

(54) BIOFILM-INHIBITING EFFECT AND ANTI-INFECTIVE ACTIVITY OF N,C-LINKED ARYL ISOQUINOLINES AND THE USE THEREOF

(75) Inventors: Gerhard Bringmann, Würzburg (DE); Tanja Gulder, San Diego, CA (US); Ute Hentschel, Würzburg (DE); Frank Meyer, Würzburg (DE); Heidrun Moll, Würzburg (DE); Joachim Morschhäuser, Erlabrunn (DE); Alicia Ponte-Sucre De Vanegas, Würzburg (DE); Wilma Ziebuhr, Veitshöchheim (DE); August Stich, Gerbrunn (DE); Reto Brun, Therwil (CH); Werner E. G. Müller, Wiesbaden (DE); Virima Mudogo, Kinshasa (CD)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 202 days.

(21) Appl. No.: 12/443,318

(22) PCT Filed: Sep. 27, 2007

(86) PCT No.: PCT/EP2007/008440
§ 371 (c)(1),
(2), (4) Date: Oct. 6, 2009

(87) PCT Pub. No.: WO2008/037482
PCT Pub. Date: Apr. 3, 2008

(65) Prior Publication Data
US 2010/0286198 A1  Nov. 11, 2010

(30) Foreign Application Priority Data
Sep. 27, 2006 (DE) .................. 10 2006 046 922

(51) Int. Cl.
*A61K 31/47* (2006.01)
*C07D 217/00* (2006.01)
(52) U.S. Cl. ....................... 514/307; 546/139
(58) Field of Classification Search .................. 514/307; 546/139
See application file for complete search history.

(56) References Cited

U.S. PATENT DOCUMENTS
6,846,839 B1 * 1/2005 Tang et al. .................. 514/397

OTHER PUBLICATIONS
Ponte-Sucre et al, Antimicrobial Agents and Chemotherapy, 2006, 51(1): 188-194.*
Zhang et al. CAS: 145: 271617, 2006.*
Yang et al. CAS: 139:273696, 2003.*
Beke et al. CAS: 58:33330, 1963.*
Bringmann et al., "Ancisheynine, the first N, C-Coupled Naphthylisoquinoline Alkaloid: Total Synthesis and Stereochemical Analysis", *Organic Letters*, 2006, vol. 8, No. 6, pp. 1037-1040.
Ponte-Sucre et al., "Activities of Naphthylisoquinoline Alkaloids and Synthetic Analogs against *Leishmania major*", *Antimicrobial Agents and Chemotherapy*, 2007, vol. 51, No. 1, pp. 188-194.
Yang et al., "Ancisheynine, a novel naphthylisoquinolinium alkaloid from *Ancistrocladus heyneanus*", *Tetrahedron Letters*, 2003, vol. 44, No. 31, pp. 5827-5829.
Zhang et al., "Superacid-Promoted Reactions of N-Acyliminium Ions: An Effective Route to Substituted 3-Oxo-1,2,3,4-tetrahydroisoquinolines and Related Products", *Synthesis*, 2006, No. 11, pp. 1775-1780.

* cited by examiner

*Primary Examiner* — Rei-tsang Shiao
(74) *Attorney, Agent, or Firm* — Saliwanchik, Lloyd & Eisenschenk

(57) ABSTRACT

Anti-infective and biofilm-inhibiting activities of aryl isoquinoline-derivatives of the general formulae 1 to 3

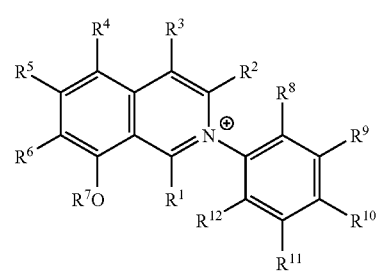

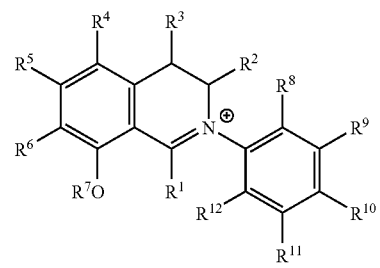

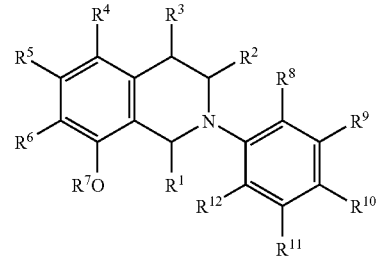

are described.

17 Claims, 1 Drawing Sheet

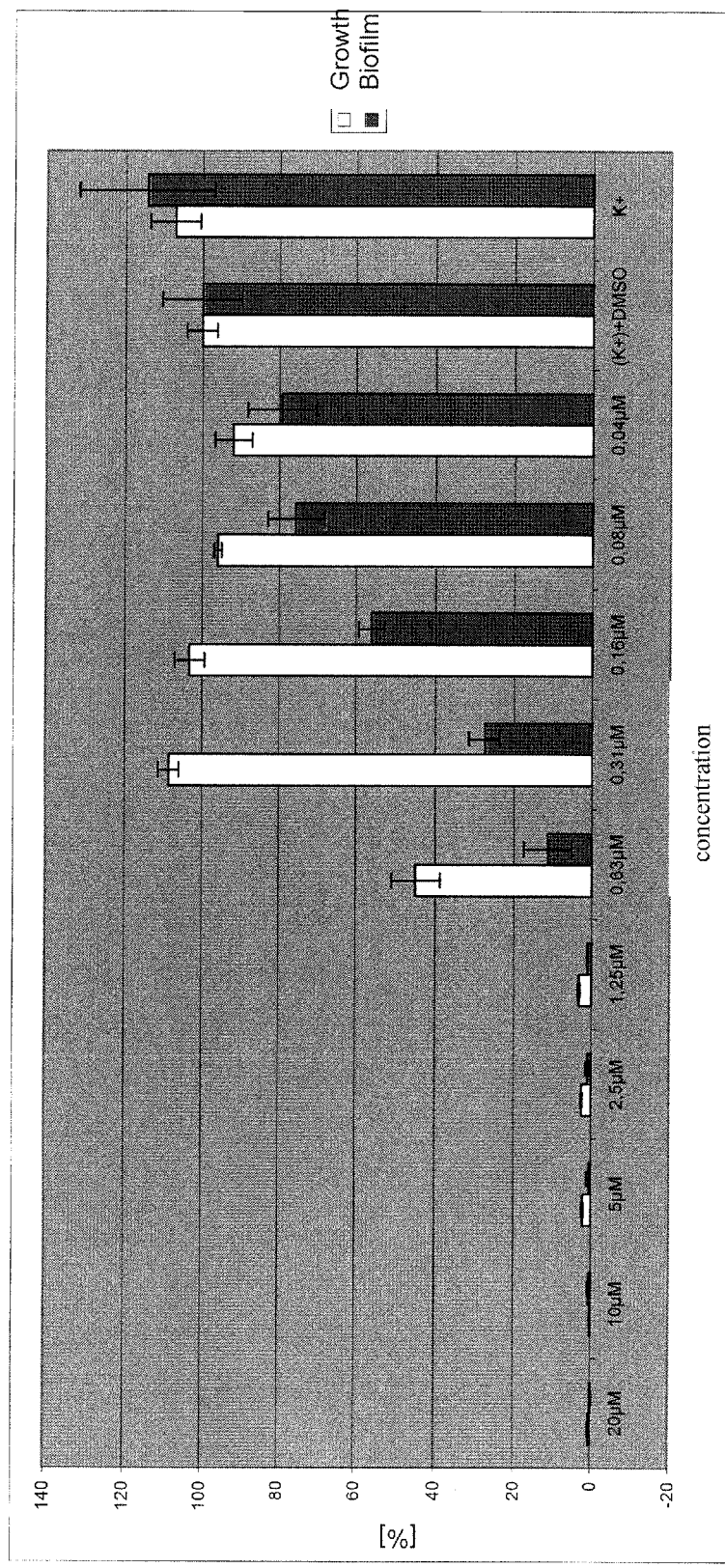

BIOFILM-INHIBITING EFFECT AND ANTI-INFECTIVE ACTIVITY OF N,C-LINKED ARYL ISOQUINOLINES AND THE USE THEREOF

CROSS-REFERENCE TO A RELATED APPLICATION

This application is a National Stage Application of International Application Number PCT/EP2007/008440, filed Sep. 27, 2007; which claims priority to Germany Patent Application No. 10 2006 046 922.4, filed Sep. 27, 2006; all of which are incorporated herein by reference in their entirety.

The present invention relates to the anti-infective (anti-candida, anti-leishmania, antitrypanosoma, anti-plasmodium) as well as biofilm-inhibiting activities of N,C-bonded aryl isoquinoline-derivatives and their uses, in particular as bioactive drugs for biotechnological and medical uses, especially for the prevention of the formation of biofilms by human pathogenic bacteria, and the anti-infective potential of specific members of said compounds against the pathogens plasmodia, trypanosoma, and leishmania.

BACKGROUND OF THE INVENTION

According to the report on world health 2002 of the World Health Organization (WHO), world-wide infectious diseases still are the main cause of death. In particular in the developing countries each year millions of people die from the implications of malaria, sleeping sickness, Chagas-disease, leishmaniosis, candida-infections and other infectious diseases. Whereas in the industrialized countries the classical infectious diseases initially appeared to be defeated (2002: 7% of the fatal cases in Germany), these are progressing world-wide again: Many of the common drugs loose their effect because of the increasing resistance of the pathogens. These also include Gram-positive bacteria, such as staphylococci and enterococci that can cause septicemia and other infections, mainly in immune-suppressed patients. The methicillin and oxacillin-resistant staphylococci (MRSA, ORSA), the vancomycin-resistant enterococci, and the multi-resistant pseudomonades are to be mentioned as particularly problematic germs.

In addition to the increasing generation of resistance of microbial pathogens, their formation of biofilms is a large problem. Biofilms are understood as a community of microorganisms that is coated with an extracellular polysaccharide or protein-matrix, whereby the individual cells are able to stick to another and/or to surfaces (J. W. Costerton, Z. Lewandowski, D. E. Caldwell, D. R. Korber, H. M. Lappin-Scott, *Annu. Rev. Microbiol.* 1995, 49, 711-745; P. Stoodley, K. Sauer, D. G. Davies, J. W. Costerton, *Annu. Rev. Microbiol.* 2002, 56, 187-209).

Thereby, the microbial community can be composed of one or even several species. The organization of cells in a biofilm leads to a markedly increased resistance of the overall population against a large variety of influences. Thus, biofilms are not to be understood as a group of individual cells. Rather, they are similar in their physiology to a multicellular organism, in which a different gene expression and metabolic activity, dynamics, and division of labor is found.

Biofilms are widely found in nature. They can be preferably found at the interfaces between the solid and liquid phase, and possibly are the primary life-form of microorganisms in the aquatic milieu (rivers, lakes, oceans, etc.). They also cause an essential economic damage in shipping through the formation of biofilms on those parts of ships that are located under water. Then, these are the organic matrix for the further growth of mussels or bryozoans. This secondary growth on of the hull of ships can reach a thickness of several decimeters, and leads to a drastic increase of the drag of water and thus to a reduction of the maneuverability and the speed of the ships, and to an increased consumption of fuel. Nevertheless, biofilms can also become a threat for humans. Indeed, biofilm-forming human pathogenic bacteria represent an important cause for chronic and recurring infections in human medicine. Prominent examples for this are the formation of plaque on teeth by streptococci, the formation of alginate of *Pseudomonas aeruginosa* in lung infections in the context of a cystic fibrosis, and, last but not least, the colonization of plastic and metal implants by biofilm-forming staphylococci in modern intensive care medicine.

In view of the increasing importance of nosocomial infections, we have concentrated our attempts on the identification of biofilm-inhibiting drugs against multi-resistant *Staphylococcus-aureus* and *S.-epidermidis*-pathogens. These bacteria mainly occur in connection with the use of plastic and metal implants. In particular in immune-suppressed patients they can cause severe general infections that are mainly caused by *Staphylococcus epidermidis* and *Staphylococcus aureus*. Both species form biofilms on artificial surfaces (e.g. on venous catheters, pacemakers or on joint replacements) that consist of the bacteria themselves and a polysaccharide matrix. This matrix, which is also designated as Polysaccharide-Intercellular-Adhesin (PIA), consists of β-1,6-bonded glucosaminoglycane-subunits that are substituted with different side groups (D. Mack, W. Fischer, A. Krokotsch, K. Leopold, R. Hartmann, H. Egge, R. Lauts, *J. Bacteriol.* 1996, 178, 175-183). The substance mediates the adherence of the cells with another, and thus is responsible for the three-dimensional, multi-layered growth of a staphylococcal biofilm. Until today, four proteins, IcaA, IcaD, IcaB, and IcaC, could be identified that are involved in PIA-synthesis (C. Hellmann, O. Schweitzer, C. Gerke, N. Vanittanakom, D. Mack, F. Götz, *Mol. Microbial.* 1996, 20, 1083-1091; C. Gerke, A. Kraft, R. Süssmuth, O. Schweitzer, F. Götz, *J. Biol. Chem.* 1998, 29, 18586-18593). The genes that encodes for these enzymes are organized in the so-called icaADBC-operon, which so far was identified in all *S.-aureus*-isolates as tested, and in 70 to 80 percent of all *S.-epidermidis*-strains from foreign matter-associated infections (W. Ziebuhr, C. Heilmann, F. Götz, P. Meyer, K. Wilms, E. Straube, J. Hacker, *Infect. Immun.* 1997, 65, 890-896; S. E. Cramton, C. Gerke, N. F. Schnell, W. W. Nichols, F. Götz, *Infect. Immun.* 1999, 67, 5427-5433).

Although the PIA, according to all findings so far, is the most important factor for the generation of a biofilm in staphylococci, nevertheless, also additional components are involved in this. It was shown that the establishment of a biofilm takes place in two phases. The first phase first requires the adherence of the staphylococci on the surface, in the second phase followed by the PIA-mediated accumulation of the biofilm. The first phase of the formation of the biofilm, which is also designated as initial adherence, is mediated in *S. epidermidis* by a surface protein, which is known as AtlE (C. Heilmann, M. Hussain, G. Peters, F. Götz, *Mol. Microbial.* 1997, 24, 1013-1024). In addition to the initial adherence, AtlE also has another function in the cell of the *staphylococcus*. It is involved as autolysin-protein in the separation of the cell wall during cellular division. Mutations in the atlE-gene thus lead to an inhibition of the formation of biofilms on surfaces and to a generation of cellular aggregates in the supernatant of the culture (C. Heilmann, M. Hussain, G. Peters, F. Götz, *Mol. Microbial.* 1997, 24, 1013-1024). Most recently, additional factors were detected that are involved in the formation of biofilms of staphylococci. Members of these are teichoic acids that make up for an essential part of the biofilm-matrix (I. Sadovskaya, E. Vinogradov, S. Flahaut, G. Kogan, S. Jabbouri, *Infect Immun* 2005, 73, 3007-3017.) Similarly, two surface-associated proteins, Aap and Bap, were identified that can mediate the accumulative phase of the formation of biofilms independently of ica and PIA (H. Rohde, C. Burdelski, K. Bartscht et al., *Mol. Microbial.* 2005, 55, 1883-1895; C. Cucarella, C. Solano, J. Valle, B. Amorena, I. Lasa, J. R. Penades, *J. Bacterial.* 2001, 183, 2888-2896.)

Furthermore, for some of the compounds an outstanding activity against trypanosomes could be found. These single-cell parasites are important pathogens in the veterinary, but especially in human, medicine. According to information provided by the World Health Organization, every year 300.000 to 500.000 humans suffer from sleeping sickness that is caused by *trypanosoma brucei* (A. Stich, P. M. Abel, S. Krishna, *BMJ.* 2002, 325, 203-206). Without therapy, the disease ends fatally. The medicaments as currently available have a lot of side effects, can not be obtained everywhere, and often are not effective enough. Therefore, new medical options are urgently needed (A. Stich, M. P. Barrett, S. Krishna *Trends Parasit.* 2003, 19, 195-197).

It is therefore an object of the present invention to provide novel, highly effective and non-toxic substances, which, in particular, can be used for an improved inhibition of the formation of biofilms, as well as for a treatment of diseases, such as, for example, infectious diseases.

This object is solved by the N,C-bonded aryl isoquinolines of the general formulae 1 to 3,

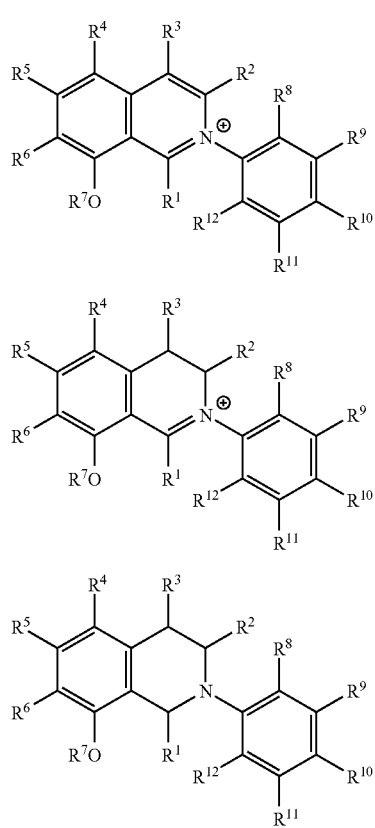

wherein $R^1$ to $R^6$ and $R^8$ to $R^{12}$ independently are either H, a non-substituted, monosubstituted or polysubstituted $C_1$-$C_{18}$-alkyl, wherein the alkyl can be straight, branched or cyclic, alkenyl, a non-substituted, monosubstituted or polysubstituted aryl or heteroaryl residue, a non-substituted, monosubstituted or polysubstituted benzyl group, an acyl group, such as, for example, formyl, acetyl, trichloroacetyl, fumaryl, maleyl, succinyl, benzoyl, or a branched or heteroatom- or aryl-substituted acyl group, an alkoxy substituent, such as, for example, —OMe, —OEt, —OnPr, -iPr, —OnBu, —OiBu, —OsecBu, —OtBu, the alkyl group thereof is branched, non-branched or cyclic, an alkyl group bound through a sulfur atom, such as, for example, —SMe, —SEt, or a sulfonyl group, such as, for example, —SO$_3$H, —SO$_2$Me, —SO$_2$CF$_3$, —SO$_2$C$_6$H$_4$CH$_3$ or SO$_2$C$_6$H$_4$CH$_2$Br, or a nitrogen substituent, such as, for example, —NH$_2$, —NHR, —NRR' (with R, R'=alkyl, aryl etc.), —NC or —NO$_2$, or fluoro, chloro, bromo, iodo, —CN or a hetero substituent, $R^7$ independently can be either H, a non-substituted, monosubstituted or polysubstituted $C_1$-$C_{18}$-Alkyl, wherein the alkyl can be straight, branched or cyclic, a monosubstituted or polysubstituted, straight, branched or cyclic $C_1$-$C_{18}$-alkenyl or can be an acyl group, such as, for example, formyl, acetyl, trichloroacetyl, fumaryl, maleyl, succinyl, benzoyl, branched or heteroatom- or aryl-substituted acyl groups, and $R^8$ to $R^{12}$ can also be bonded in a manner that thereby a non-substituted, monosubstituted or polysubstituted ring and dimers of 1 is generated, as well as pharmaceutically acceptable salts or solvates, with the proviso that the following substances are excluded from the above-mentioned compounds according to the invention:

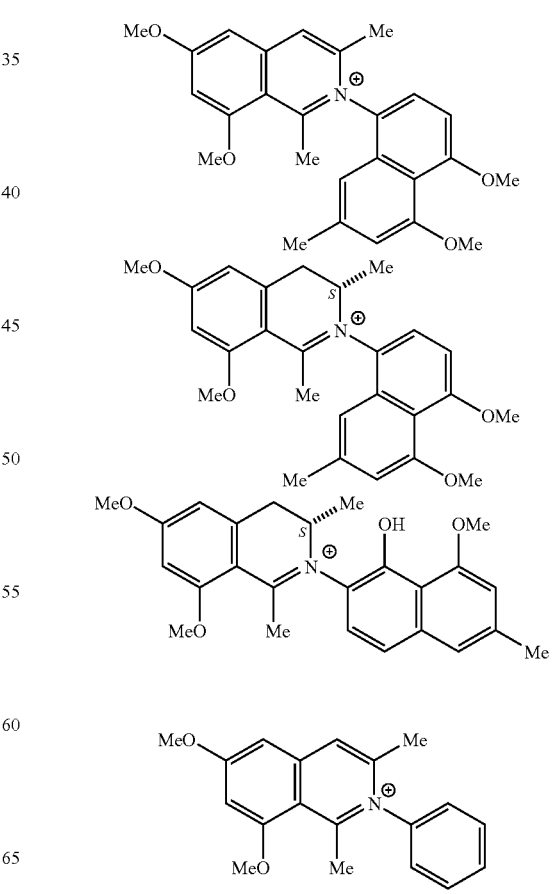

-continued

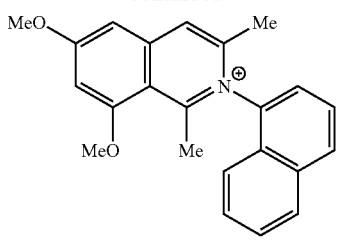

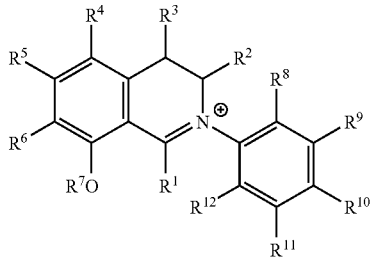

In view of the increasing importance of hospital-derived infections, the inventors have concentrated their efforts on the identification of novel drugs against multi-resistant *Staphylococcus-aureus* and *S.-epidermidis* pathogens, since these are responsible for the largest number of hospital-derived infections. Thereby, not only the approach of searching for those that are effective in the bacteriostatic or bactericidal killing of the pathogens, but particularly those compounds are sought for that interfere with the gene regulation and gene expression of virulence factors. This concept appears to be reasonable in particular with foreign matter-associated staphylococcal infections. Staphylococci form biofilms on plastic and metal surfaces of medical implants, thus representing a major source for persisting and recurring infections. A prevention of the formation of biofilms or their dissolution and removal would markedly contribute to a therapy of nosocomial infections.

A further aspect of the present invention relates to the use of a series of the above-mentioned compounds for a treatment of infectious diseases, such as leishmaniosis and trypanosomal diseases (such as the African sleeping sickness or Chagas-disease). Indeed, it could be found that, upon a modification of the different structural parameters, conveniently the selectivity of the activity can be improved, particularly against a specific pathogen.

A medical applicability of the compounds of the general formulae 1 to 3 as identified according to the present invention was yet unknown. A further aspect of the present invention thus relates to their use for a prevention or treatment of diseases, such as, for example, tumorous diseases or infectious diseases.

A further aspect of the present invention then relates to the use of a compound of the general formulae 1 to 3:

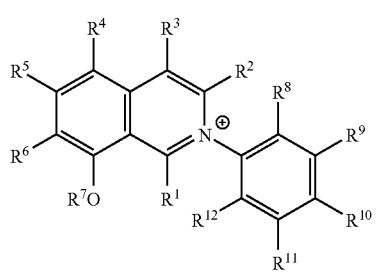

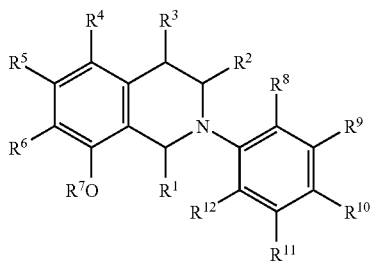

wherein the residues $R^1$ to $R^{12}$ are as defined above, for an inhibition of the formation of biofilms on surfaces. Preferably, the use relates to an inhibition of the formation of biofilms through staphylococci, such as, for example, *S. epidermidis*, on plastic and metal surfaces of medical implants, stents, catheters, cannulae, and other medical invasive devices.

A further aspect of the invention relates to the use of the compounds according to the present invention as tools for studying and research of the formation of biofilms, and as "Lead Structures" for the development of additional compounds that inhibit the formation of biofilms and are anti-infective.

In the context of the present invention, a "derivative" shall be a compound derived from the general formulae 1 to 3, which, for example, is substituted in several of the residues as given above for $R_1$ to $R_{12}$, as well as mixtures of several of these compounds, which, for example, can be converted into a medicament that can be "personalized" for the disease to be treated and/or the patient, respectively, on the basis of diagnostic data or data with respect to the success of the therapy or progress thereof.

A "precursor" of a substance in the context of the present invention shall mean, on the one hand, a substance which during the course of its administration for a treatment is modified by the conditions in the body (e.g. pH in the stomach, or the like) in such a way, or after uptake is metabolized by the body in such a way, that the compounds of the invention or their derivatives are formed as effective substances.

The invention shall now be further described in the following with reference to the attached FIGURE, nevertheless, without being limited thereto.

EXAMPLE 1

Synthesis of the Isoquinolinium-Salt A (=Formula 1a)

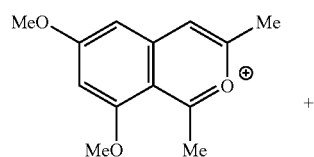

4

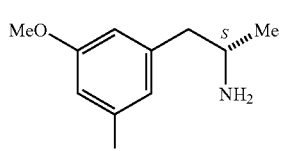

5

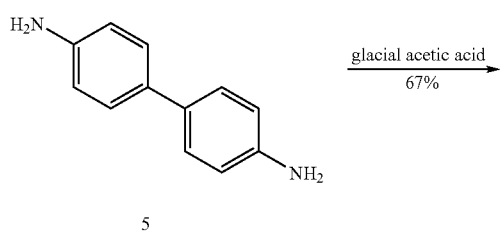

1a 200 mg (0.628 mmol) of the benzopyrylium-salt 4 (produced according to G. Bringmann, *Liebigs Ann. Chem.* 1985, 2126-2134) were dissolved in 5 ml glacial acetic acid, 57.9 mg (0.314 mmol) of benzidine (5) were added, and were stirred over night at room temperature. After reaction was finished, 5 ml of diethylether were added to the suspension, and the precipitated solid was removed by suction. The solvent of the mother liquor was removed in vacuo, and the oily residue was purified using column chromatography on Sephadex-LH20 (methanol+5% trifluoro acetic acid). The isoquinolinium-salt A is obtained in the form of beige needles.

N,N'-(1,1'-benzidine)-di-(6,8-dimethoxy-1,3-dimethylisoquinolinium)-salt (A)

Yield: 171 mg (0.210 mmol; 67%).
Melting point: >350° C. (methanol)
IR (KBr): $\tilde{v}$=3409 (br), 2949 (m), 2823 (w), 1687 (m), 1643 (m), 1612 (s), 1559 (m), 1494 (w), 1466 (m), 1387 (s), 1288 (w), 1201 (s), 1116 (s), 1027 (m), 970 (w), 837 (w), 799 (w) cm$^{-1}$.
$^1$H-NMR (400 MHz, DMSO): δ=2.29 (s, 6H, 3-CH$_3$), 2.91 (s, 6H, 1-CH$_3$), 4.17 (s, 12H, OCH$_3$), 7.09 (d, $^4$J=2.15 Hz, 2H, Ar—H), 7.21 (d, $^4$J=2.15 Hz, 2H, Ar—H), 7.78 (d, $^3$J=8.59 Hz, 4H, Ar—H), 8.15 (s, 2H, Ar—H), 8.28 (d, $^3$J=8.59 Hz, 4H, Ar—H) ppm.
$^{13}$C-NMR (100 MHz, DMSO): δ=21.63 (CH$_3$), 23.27 (CH$_3$), 56.62 (OCH$_3$), 57.12 (OCH$_3$) 98.93, 102.2, 110.19, 121.68, 127.45, 129.10, 139.41, 140.21, 141.78, 144.05, 159.45, 161.36, 166.79 (Ar—C) ppm.
MS (70 eV): m/z (%) 586 (14) [M]$^+$, 369 (10), 353 (8), 293 (24), 264 (8), 69 (13), 44 (49).
C$_{38}$H$_{38}$N$_2$O$_4$ (HRMS): Calc. 586.2823; Found 586.2785.

EXAMPLE 2

Synthesis of the Dihydro Isoquinolinium-Salt 2a

Production of the Secondary Amine (S)-8

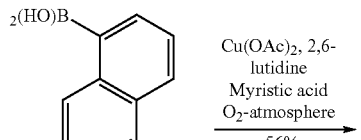

6

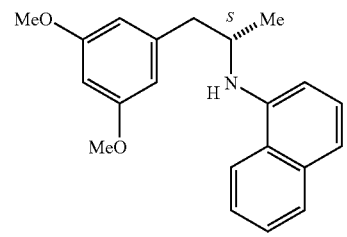

7

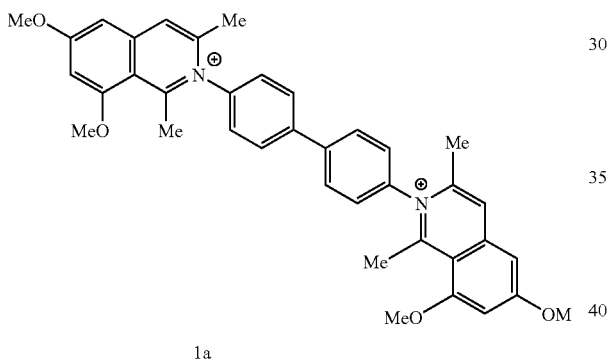

8

272 mg (2.55 mmol) of 2,6-lutidine were added to a suspension consisting of 658 mg (3.83 mmol) of 1-naphthyl boric acid (7), 0.926 mg (0.005 mmol) copper(II) acetate, and 1.14 mg myristic acid in 5 ml absolutized toluene. After 5 minutes, 500 mg (2.55 mmol) of primary amine 6 (produced according to G. Bringmann, R. Weirich, H. Reuscher, J. R. Jansen, L. Kinzinger, T. Ortmann *Liebigs Ann. Chem.* 1993, 877-888) were added, and the reaction mix was stirred for 30 hours in an oxygen atmosphere at room temperature. Subsequently, the suspension was diluted with 10 ml acetic ethyl ester, and filtered through silica (acetic ethyl ester). The solvent was removed in vacuo, and the product was purified using column chromatography (silica, petrolether:ethyl acetate=10:1). The secondary amine 8 was obtained as a brown oil.

(2R)—N-(1-naphthyl)-1-(3',5'-dimethoxyphenyl)-2-aminopropane (S)-8

Yield: 459 mg (1.43 mmol; 56%).
Rotation value: $\alpha_D=47°$ (c=0.10, dichloromethane)
IR (KBr): $\tilde{v}$=3417 (br), 3098 (m), 2997 (m), 2918 (w), 1595 (s), 1523 (w), 1459 (m), 1406 (w), 1385 (w), 1276 (m), 1203 (m), 1149 (s), 1082 (w), 792 (w), 769 (s) cm$^{-1}$.
$^1$H-NMR (400 MHz, MeOD): $\delta$=1.32 (d, $^3J$=6.44 Hz, 3H, CH$_3$), 2.85 (dd, $^3J$=13.26 Hz, $^2J$=7.08 Hz, 1H, CH$_2$), 3.00 (dd, $^3J$=13.27 Hz, $^2J$=5.30 Hz, 1H, CH$_2$), 3.69 (s, 6H, OCH$_3$), 3.98 (m, 1H, CH), 6.31 (t, 1H, Ar—H), 6.43 (d, $^4J$=2.27 Hz, 2H, Ar—H), 6.74 (d, $^3J$=7.58 Hz, 1H Ar—H), 7.18 (d, $^3J$=8.21 Hz, 1H, Ar—H), 7.34 (t, 1H, Ar—H), 7.42 (m, 2H, Ar—H), 7.77 (dd, $^3J$=9.47 Hz, $^4J$=2.02 Hz, 1H, Ar—H), 7.96 (dd, $^3J$=6.57 Hz, $^4J$=1.64 Hz, 1H, Ar—H) ppm.
$^{13}$C-NMR (100 MHz, MeOD): $\delta$=20.48 (CH$_3$), 43.10 (CH$_2$), 50.87 (CH), 55.73 (OCH$_3$), 99.50, 106.1, 108.7, 117.8, 121.9, 125.3, 125.4, 126.7, 127.8, 129.5, 136.3, 142.8, 144.3, 162.4 (Ar—C) ppm.
MS (70 eV): m/z (%) 322 (2) [M+H]$^+$, 221 (10) [M]$^+$, 234 (2), 170 (100), 154 (6), 128 (7), 115 (3), 91 (2), 77 (3), 42 (2).
C$_{21}$H$_{24}$NO$_2$ (HRMS): Calc. 322.18070; Found 322.18043.

Production of the Amide (S)-9

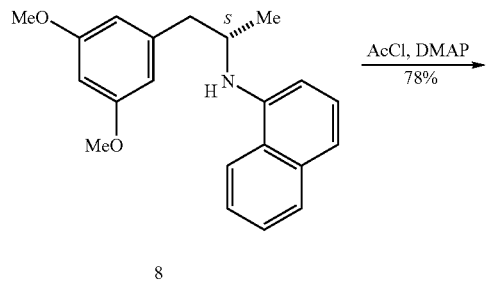

8

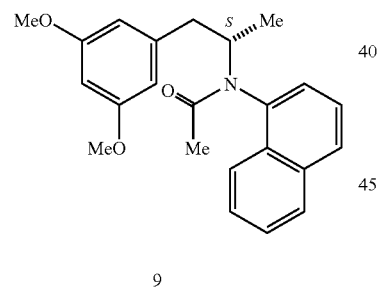

9

138 mg (1.76 mmol) acetylchloride were added drop-wise at room temperature under a protective gas atmosphere to a solution consisting of 256 mg (0.731 mmol) secondary amine 8 and 120 mg (0.877 mmol) DMAP in 15 ml toluene, and were heated for 12 hours under reflux. The cooled reaction mix was spiked with water, and extracted with acetic ethyl ester. The combined organic phases were dried with MgSO$_4$, and the solvent removed in vacuo. The residue was chromatographed on silica with petrol ether:acetic ethyl ester (3:1). The amide 9 was obtained in form of its two conformers (1:0.7) in the form of beige platelets.

(2R)—N,N-(1-naphthyl-acetyl)-1-(3',5'-dimethoxyphenyl)-2-aminopropane (S)-9

Yield: 223 mg (0.615 mmol; 84%)
Melting point: 115° C. (petrol ether:acetic ethyl ester)
Rotation value: $\alpha_D=18°$ (c=0.10, methanol)
IR (KBr): $\tilde{v}$=3428 (br), 2961 (s), 2838 (w), 1657 (s), 1593 (s). 1507 (w), 1463 (s), 1428 (m), 1399 (m), 1380 (m), 1341 (w), 1320 (w), 1282 (s), 1240 (m), 1204 (m), 1159 (s), 1054 (m), 1016 (m), 926 (w), 837 (m), 805 (m), 782 (s), 684 (m), 601 (s) cm$^{-1}$.
$^1$H-NMR (400 MHz, CDCl$_3$): $\delta$=0.78 (d, $^3J$=6.94 Hz, 3H, CH$_3$), 0.95 (d, $^3J$=6.94 Hz, 2H, CH$_3$), 1.70 (s, 5H, CH$_3$CO), 2.25 (dd, $^3J$=13.01 Hz, $^2J$=9.98 Hz, 0.7H, CH$_2$), 2.54 (dd, $^3J$=12.63 Hz, $^2J$=9.98 Hz, 1H, CH$_2$), 3.19 (dd, $^3J$=13.01, $^2J$=5.43 Hz, 0.7H, CH$_2$), 3.31 (dd, $^3J$=12.75 Hz, $^4J$=4.29 Hz, 1H, CH$_2$), 3.72 (s, 4.2H, OCH$_3$), 3.81 (s, 6H, OCH$_3$), 4.89 (m, 0.7H, CH), 5.09 (m, 1H, CH), 6.27 (d, $^4J$=2.02 Hz, 1.4H, Ar—H), 6.26 (t, 0.7H, Ar—H), 6.32 (t, 1H, Ar—H), 6.49 (d, $^4J$=2.28, 1H, Ar—H), 7.13 (d, $^3J$=6.19 Hz, 0.7H, Ar—H), 7.29 (d, $^4J$=1.01 Hz, 1H, Ar—H), 7.42-7.60 (m, 5H, Ar—H), 7.81-7.99 (m, 5H, Ar—H) ppm.
$^{13}$C-NMR (100 MHz, CDCl$_3$): $\delta$=16.79 (CH$_3$), 19.24 (CH$_3$), 23.18 (CH$_3$), 23.33 (CH$_3$), 41.78 (CH$_2$), 43.54 (CH$_2$), 55.63 (OCH$_3$), 55.70 (OCH$_3$), 55.72 (CH), 57.55 (CH). 99.56, 99.63, 108.2, 108.3, 124.11, 124.12, 126.71, 126.74, 127.7, 127.8, 128.31, 128.37, 128.41, 128.5, 129.7, 129.8, 30.3, 130.4, 132.9, 133.3, 136.18, 136.20, 137.6, 138.6, 142.56, 142.63 ppm.
MS (70 eV): m/z (%) 363 [M]$^+$ (2), 185 (76), 170 (100), 156 (32), 143 (38), 127 (23), 115 (15), 49 (17), 43 (38).
C$_{23}$H$_{25}$NNaO$_3$ (HRMS): Calc. 386.17266; Found 386.17270.

Production of the Dihydro Isoquinolinium-Salt (S)-2a

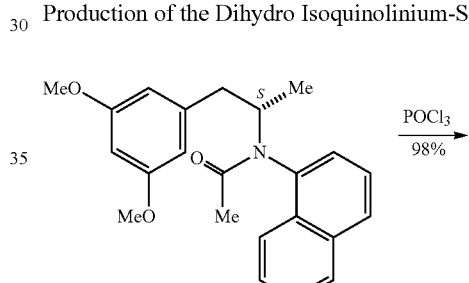

9

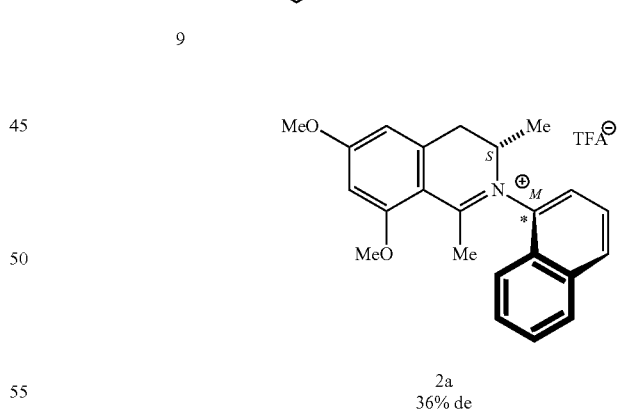

2a
36% de 0.01 ml POCl$_3$ were added to 7.00 mg of amide 9 in 2 ml absolute acetonitrile at room temperature, and heated for 1 hour at reflux. After cooling of the reaction mix to room temperature, water+TFA (1%) was added to the reaction mix, and the acetonitrile was removed in vacuo. The remaining aqueous suspension was extracted with acetic ethyl ester, the organic phases combined, dried with MgSO$_4$, and the solvent removed. The residue was purified using gel chromatography (Sephadex, methanol), whereby the isoquinolinium-salt (M)-2a and its atrop diastereomere (P)-2a (1:0.4) were obtained as yellow oil. Both diastereomeres could be separated using HPLC (Waters Symmetry C18, 45% water+0.05% TFA, 55% methanol+0.05% TFA, isocratic, 0.7 ml/min: $t_R$=8.1 min (M-2a), $t_R$=8.7 min (P-2a)).

(3S)—N,1'-naphthyl-6,8-dimethoxy-1,3-dimethyl-3,4-dihydroisoquinolinium-trifluoro-acetate (M)-2a and (P)-2a Yield: 8.78 mg (0.019 mmol; 98%)
Rotation value: $\alpha_D$=6° (c=0.25, methanol)
IR (KBr): $\tilde{v}$=3437 (br), 3020 (m), 2934 (m), 2843 (w), 1650 (s), 1595 (s), 1508 (w), 1462 (m), 1428 (m), 1379 (m), 1323 (m), 1288 (m), 1204 (m), 1152 (s), 1057 (m), 928 (w), 833 (w), 807 (m), 780 (s), 686 (m) cm$^{-1}$.
$^1$H-NMR (400 MHz, MeOD): δ=1.29 (d, $^3$J=6.82 Hz, 1.3H, 3-CH$_3$), 1.40 (d, $^3$J=6.83 Hz, 3H, 3-CH$_3$), 2.52 (s, 1.3H, 1-CH$_3$), 2.58 (s, 3H, 1-CH$_3$), 3.21 (dd, J=16.8 Hz, J=2.53 Hz, 1H, CH$_2$), 3.27 (dd, J=20.97 Hz, J=4.67 Hz, 0.4H, CH$_2$), 3.80 (dd, J=15.8 Hz, J=5.81 Hz, 0.4H, CH$_2$), 3.96 (dd, J=16.8 Hz, J=6.19 Hz, 1H, CH$_2$), 3.98, 4.81 (s, 8.4H, OCH$_3$), 4.39 (m, 1H, CH), 4.66 (m, 0.4H, CH), 6.81 (m, 1.4H, Ar—H), 6.86 (m, 1.4H, Ar—H), 7.69-7.88 (m, 6H, Ar—H), 7.98 (d, J=8.33 Hz, 1H, Ar—H), 8.18 (m, 1.4H, Ar—H), 8.26 (d, J=8.08 Hz, 1.4 Hz, Ar—H) ppm.
$^{13}$C-NMR (100 MHz, MeOD): δ=16.79 (CH$_3$), 19.24 (CH$_3$), 23.18 (CH$_3$), 23.33 (CH$_3$), 41.78 (CH$_2$). 43.54 (CH$_2$), 55.63 (OCH$_3$), 55.70 (OCH$_3$), 55.72 (CH), 57.55 (CH). 99.56, 99.63, 108.2, 108.3, 124.11, 124.12, 126.71, 126.74, 127.7, 127.8, 128.31, 128.37, 128.41, 128.5, 129.7, 129.8, 130.1, 130.3, 130.5, 130.7, 132.3, 132.5, 134.0, 135.8, 136.5, 136.20, 138.1, 142.56, 142.1, 142.70, 142.72, 166.6, 170.8, 170.7, ppm.
MS (70 eV): m/z (%) 369 [M+Na]$^+$ (2), 353 (M+Na—CH$_4$), (3), 212 (22), 185 (52), 170 (100), 154 (7), 143 (16), 127 (5), 43 (7).
MS (ESI): 346.6

EXAMPLE 3

Synthesis of the Tetrahydro Isoquinoline 3a

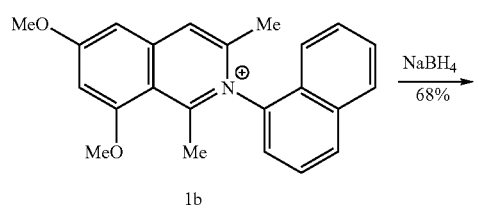

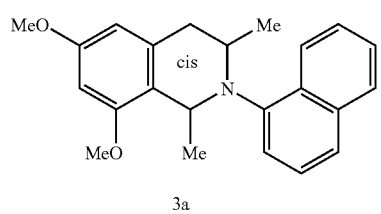

57.2 mg (0.151 mmol) of NaBH$_4$ were added in portions at 0° C. to a solution of 56.0 mg (0.126 mmol) of the isoquinolinium-perchlorate 1b in 14 ml methanol. After stirring of the reaction mix at room temperature for 1 hour, 5 ml water were added, and the stirring continued for a further 12 hours. The suspension was then spiked with half-concentrated hydrochloric acid, and the product was extracted with diethylether. The etheric phases were pooled, dried with MgSO$_4$, and the solvent removed in vacuo. The oily residue was purified on silica using column chromatography (hexane:ethyl acetate 1:2). The naphthyl tetrahydro isoquinoline 3a was obtained as white solid.

N-(1-naphthyl)-6,8-dimethoxy-1,3-(cis)-dimethyl tetrahydro isoquinoline 3a

Yield: 30.0 mg (0.103 mmol; 68%).
Melting point: 69° C. (hexane:ethyl acetate)
IR (KBr): $\tilde{v}$=3432 (br), 3043 (s), 2990 (s), 2926 (s), 2835 (m), 1687 (m), 1608 (s), 1490 (w), 1459 (m), 1423 (w), 1391 (w), 1364 (w) 1341 (w), 1321 (w), 1295 (w), 1260 (m), 1234 (w), 1207 (m), 1150 (s), 1109 (s), 1094 (s), 1049 (s), 1023 (s), 941 (w), 826 (w), 802 (m), 779 (s) cm$^{-1}$.
$^1$H-NMR (400 MHz, CDCl$_3$): δ=0.87 (d, $^3$J=6.31 Hz, 3H, 3-CH$_3$), 2.91 (d, $^3$J=6.32 Hz, 3H, 1-CH$_3$), 2.77 (dd, $^3$J=15.29 Hz, $^2$J=2.90 Hz, 1H, CH$_2$), 2.89 (dd, $^3$J=15.03 Hz, $^2$J=9.35 Hz, 1H, CH$_2$), 3.42 (m, 1H, 3-CH), 3.78 (s, 3H, OCH$_3$), 3.86 (s, 3H, OCH$_3$), 4.57 (q, 1H, 1-CH), 6.32 (d, $^4$J=2.28 Hz, 1H, Ar—H), 6.58 (d, $^4$J=2.28 Hz, 1H, Ar—H), 7.40-7.48 (m, 5H, Ar—H), 7.68 (d, $^3$J=7.71 Hz, 1H, Ar—H), 7.82 (dd, $^3$J=6.06 Hz, $^4$J=3.41 Hz. 1H, Ar—H) ppm.
$^{13}$C-NMR (100 MHz, CDCl$_3$): δ=24.11 (CH$_3$), 28.37 (CH$_3$), 39.88 (CH$_2$), 55.45 (CH), 55.89 (OCH$_3$), 56.07 (OCH$_3$), 97.34, 104.7, 109.2, 122.8, 124.8, 125.3, 125.6, 126.0, 126.3, 126.5, 126.9, 128.5, 128.7, 138.5, 157.9, 159.4 (Ar—C).
MS (70 eV): m/z (%) 347 (5) [M]$^+$, 332 (100) [M–CH$_3$], 316 (7) [M–OCH$_3$]$^+$, 189 (8) [M-naphthyl]$^+$, 127 (17) [naphthyl]$^+$, 40 (12).

| $C_{23}H_{25}NO_2$ (347.4501) | Calc. | C | 79.51 | H | 7.25 | N | 4.03 |
|---|---|---|---|---|---|---|---|
| | Found | C | 79.29 | H | 7.59 | N | 3.87 |

EXAMPLE 4

Biological Activities

1. Effect Against Parasites of the Genus *Leishmania*
*Leishmania major*-promastigotes (MHOM/IL81/FE/BNI) were cultivated in blood agar-cultures at 26° C., 5% CO$_2$, and 95% humidity. For the experiment, the promastigotes were washed twice with saline phosphate buffer (PBS) and subsequently suspended (10$^8$ cells/ml) in Click-RPMI-1640-medium without phenol red, spiked with 10% FCS, 2 mM L-glutamine, 1.0 mM HEPES-buffer, pH 7.2, 100 µg/ml penicillin, 160 mg/ml gentamycin, 7.5% NaHCO$_3$ and 50 µM 2-mercaptoethanol (culture medium). For the determination of activity, 200 µl of the promastigote-suspension in microtiter plates were each incubated with the compounds in a geometric series of dilutions for 24 hours at 26° C., 5% CO$_2$, and 95% humidity. Subsequently, 20 µl Alamar Blue (Trinova Biochem, Gießen, Germany) were added to each of the microcultures, and the cultures were incubated further. Cultures that only contained medium and the compound, or only cellular suspension (without compound), served as controls. The optical density was measured after another 24 hours with an ELISA-reader at the wave lengths 550 nm and 630 nm. The IC$_{50}$-values of the compounds were calculated through linear interpolation (J. Mikes, D. Steverding. Parasitol. Int. 2000, 48, 265-269).

Macrophages of the cell line J774.1 were washed and suspended in culture medium (2×10$^8$ cells/ml. For the test, 200 µl of the cell suspension and the compounds were pipetted in a geometric series of dilutions into cultures on microtiter plates. Following 24 hours of incubation at 37° C., 5% CO$_2$, and 95% humidity, 20 µl Alamar Blue were added to each micro-culture, and the microtiter plate was incubated further. Micro-cultures with medium and the compound as well as micro-cultures that only contained cellular suspension (without compound), served as controls. The optical density was measured after 24, 48, and 72 hours with an ELISA-reader at the wavelengths 550 nm and 630 nm. The IC$_{50}$-values of the compounds were calculated using linear interpolation. Amphotericin B served as a reference compound and positive control.

The activities of the compounds of the general structures 1-3 against *leishmania* were examined in a series of examples according to the method as described above. The therapeutic index is the ratio of cytoxicity against host cells (J774.1 macrophages) to the activity against *Leishmania major*.

2. Anti-Trypanosome Effects

Bloodstream-forms of the strain TC-221 of *Trypanosoma brucei brucei* were cultivated in enriched Baltz-culture medium in an atmosphere von 5% CO$_2$ at 37° C. For activity determinations, a defined number of pathogens (10$^4$ trypanosomes per ml) were incubated in 96-well-plates with the compounds in different concentrations for 48 to 72 hours. The effect of the drugs was quantifiable using the ED$_{50}$-values with linear interpolation. The trypanocidal activity of the test compounds was determined through measuring absorption on an MR 700 microplate reader (test wavelength 550 nm, reference wavelength 630 nm) by means of Alamar Blue®, an indicator of metabolic cellular functions. The addition of the dye took place 24 hours after starting the incubation. The color change of Alamar Blue® as used in this absorption measurements is based on reduction processes involving NADH or NADH-dependent enzymes. Incubation times and the concentrations of dye as required correlate with the metabolic activities of the trypanosomes. The MIC-value (minimum inhibitory concentration) was determined microscopically through counting of living cells in Neubauer-counting chambers. Suramine Na served both as positive control and reference.

TABLE 1

Exemplary effect against *Leishmania major* as well as their therapeutic index.

| | Examples for test compounds | IC$_{50}$ (µM) | Therapeutic index |
|---|---|---|---|
| B | [structure] | 2.45 | 13 |
| C | [structure] | 2.02 | 17 |
| D | [structure] | 0.85 | 18 |
| | Amphotericin B | 2.51 | n.d. |

The compounds as exemplary shown in Table 1 show an excellent effect against *L. major*. Here, in particular the compounds with alkyl substituents in the aryl residue show a very good and particularly selective effect against this pathogen. Thereby, compound D served as preferred lead compound, which is also suited for a further chemical derivatization.

The anti-trypanosomal activities of the compounds of the general structures 1-3 were studied based on a series of examples according to the above-described methods. The therapeutic index is the ratio of the cytoxicity (J774.1 macrophages) to the activities against *Trypanosoma brucei brucei*.

TABLE 2

Exemplary effects against *Trypanosoma brucei brucei* after 48 and 72 hours as well as their therapeutic index.

| Examples for test compounds | | ED$_{50}$ (µM) after 48 h | ED$_{50}$ (µM) after 72 h | Therapeutic index |
|---|---|---|---|---|
| E | 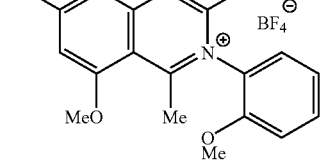 1d | 0.383 | 0.323 | 86 |
| F | 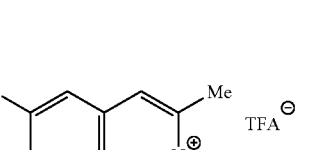 | 0.325 | 0.311 | 72 |
| 2a | 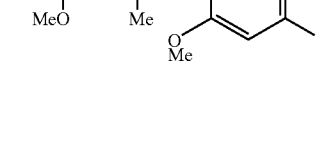 | 0.390 | 0.356 | >180 |
| Suramin Na | | 0.31 | 0.32 | n.d. |

The compounds as exemplary shown in Table 2 have a pronounced effect against T brucei brucei. Especially those compounds with electron-pushing substituents in N-aryl-substituents in the in-vitro-model exhibited a selective effect against this pathogen, at good therapeutic indices. In tests of these compounds against other cells, such as L5178Y mice lymphoma-cells, also relatively low cytotoxicities (ED$_{50}$>10 µM) could be found when the cells were held under growth conditions, in which the generation time of 12 hours is increased to 18 hours. Thereby, compound 2a served as preferred lead compound, which is also suitable for a further chemical derivatization.

3. Anti-Plasmodium Effects

For the determination of the anti-plasmodium activities, cultures of *Plasmodium falciparum* strain K1 (resistant against chloroquine and pyrimethamine) were used. A modification (R. G. Ridley, W. Hofheinz, if Matile, C. Jacquet, A. Dorn, R. Masciadri, S. Jolidon, W. F. Richter, A. Guenzi, M. A. Girometta, H. Urwyler, W. Huber, S. Thaitong, W. Peters, *Antimicrob. Agents Chemother.* 1996, 40, 1846-1854) of the [³H]-hypoxanthine-inclusion-test (R. E. Desjardins, C. J. Canfield, D. Haynes, J. Chulay, *Antimicrob. Agents Chemother.* 1979, 16, 710-718) was used. Human red blood cells infected with *P. falciparum* (0.3% infection) at a hematocrit of 2.5% (volume fraction of the red blood cells) in RPMI 1640 medium with the serum replacement Albumax II (5 g/L) were incubated with serial dilutions of the drugs in microtiter plates for 48 hours at 37° C. under a CO$_2$-enriched and O$_2$-reduced atmosphere. Then, 0.5 µCi [³H]-hypoxanthine were added to each well of the microtiter plate, and after a further 24 hours of incubation time the wells were harvested with a Betaplate Cell Harvester onto glass fiber filters, and lysed with distilled water. The incorporation of radio-labeled hypoxanthine (which correlates with the quantity of living parasites) was determined using a scintillation counter. The IC$_{50}$ value was determined from sigmoidal inhibition curves. The tests were performed in duplicate, and repeated at least once. Parasite cultures without additive served as control (100% incorporation), cultures with a dilution series of chloroquine served as positive control.

The anti-plasmodia activities of the compounds of the general structures 1-3 were studied based on a series of examples according to the above-described methods. The therapeutic index is the ratio of the IC$_{50}$ values for rat myoblasts (L-6-cells=cytotoxicity) to the IC$_{50}$ values for *Plasmodium falciparum*.

TABLE 3

Exemplary effects against *Plasmodium falciparum* as well as their therapeutic index.

| Examples for test compounds | | IC$_{50}$ (µM) | Therapeutic index |
|---|---|---|---|
| G | 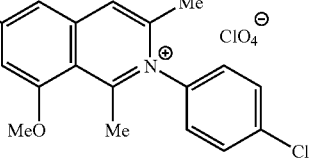 | 0.056 | 671 |
| H | 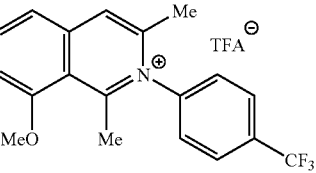 | 0.282 | 324 |
| I | 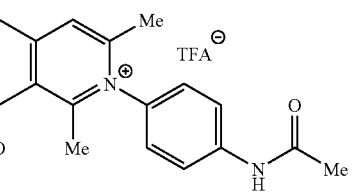 | 0.211 | >841 |
| chloroquine | | 0.119 | n.d. |

It can be seen that in particular compounds with the para-positioned acyl amido group, such as, for example, I exhibit a pronounced activity against strain K1 of *P. falciparum*, without a detectable cytotoxicity. Thereby, compound I served as the preferred lead compound, which is also suitable for a further chemical derivatization.

4. Growth-Inhibiting Effect (Exemplary for A (See Example 1) on Gram-Positive Bacteria of the Genus *Staphylococcus* and Yeasts of the Species *Candida albicans*

Use: a) Therapy and prevention of infections through Gram-positive bacteria and pathogenic yeasts in human and veterinary medicine; b) Conservation of foods, medicines and cosmetics through lowering the germ load and/or prevention of the colonialization through Gram-positive bacteria and yeasts.

Examination of the Inhibitory Effect Through Determining of the Minimal Inhibitory Concentration (MIC) in the Micro-Bouillon-Dilution Methods The MIC (minimal inhibitory concentration) is the lowest concentration of an antibiotic compound (in µM or µg/ml) which under experimental conditions still barely inhibits the growth of the pathogen. In this method, a series of dilutions with decreasing concentrations of drug is produced in 96-well-microtiter plates from a stock solution of the compound. The drug-containing microtiter plate-wells are inoculated with a defined amount of the pathogen to be tested, and cultivated. The concentration of the compound in the well, where no more turbidity of the medium due to a growth of the pathogens could be optically detected is given as the MIC.

Technique

The test strains were inoculated in Luria-Bertani-medium, and grown over night in a shaking incubator at 37° C. until stationary growth phase. On the following day, the culture was diluted 1:100 with fresh Müller-Hinton-bouillon (MH-Medium) containing 5% NaCl (w/v), and until logarithmic growth phase incubated again at 37° C. inkubiert. The optical density of the bacterial suspension was photometrically measured at 550 nm, and the suspension adjusted at 2×10$^5$ colony forming units/ml (CFU/ml). In the meantime, a geometric series of dilutions of the test compounds was produced in MH-medium. 100 µl of each dilution were pipetted into the corresponding wells of a 96-well-polystyrene-flat bottom-microtiter plate. The plates were inoculated with 100 µl of the pre-prepared inoculum, and cultured in the incubator for 18 hours at 37° C. On the following day, the optical density of the bacterial cultures in the wells was determined with an ELISA-reader at a wavelength of 550 nm, compared to the blank value (=non-inoculated MH-medium). The concentrations of the compound in the last wells, wherein no more growth of the pathogens could be detected, is given as the MIC. A low MIC indicates a high inhibitory activity of a compound, whereas a high concentration indicates a low activity.

Results

The MIC of, for example, A was tested for the following germs and strains:

*Staphylococcus aureus* 325: Biofilm-positive clinical isolate from blood culture, wild type

*Staphylococcus aureus* NCTC 8325: Biofilm-negative reference strain, genome published

*Staphylococcus epidermidis* RP62A: Biofilm-positive, multi resistant reference strain

*Escherichia coli* 536: urinary tract isolate, reference strain

*Pseudomonas aeruginosa*: environmental isolate

*Candida albicans* 5314: clinical isolate

TABLE 4

Minimal inhibitory concentrations of A against several infectious pathogens

| Strain | Minimal inhibitory concentrations ($\mu M$) |
| --- | --- |
| Staphylococcus aureus 325 | 0.63 |
| Staphylococcus aureus NCTC 8325 | 5.00 |
| Staphylococcus epidermidis RP62A | 0.63 |
| Escherichia coli 536 | 20.00 |
| Pseudomonas aeruginosa | >160 |
| Candida albicans 5314 | 1.25 |

Determination of the Cytotoxicity by the Alamar-Blue®-Assay with the Example of Substance A The cytotoxicity of A was determined by means of an Alamar-Blue®-assay. First, a geometric series of dilutions of A in cellular medium (293 kidney epithelial cells; without phenol red) with 1% DMSO was produced, and in a 96-well-polystyrol-flat bottom-microtiter plate vorgelegt. The cells were trypsinized, and washed once. For the test, a cellular suspension of $10^5$ cells/ml was prepared, and 20 µl thereof were pipetted into the wells. The final volume was 200 µl. After 24 h incubation at 37° C. and 5% $CO_2$, 20 µl Alamar Blue (Trinova Biochem, Gießen, Germany) was added into each well, and the microtiter plate was incubated further. The wells that contained the medium and substance, as well as those that only contained cellular suspension (without substance), served as negative or positive control, respectively. The optical density was measured after 24 h and 48 h with an ELISA-reader at the wavelengths 550 nm and 630 nm. The $IC_{50}$ value for A was calculated following linear interpolation (W. Huber, J. C. Koella Acta Tropica 1993, 55, 257-261).

TABLE 5

Cytotoxicity of A and its therapeutic index against both biofilm-forming staphylococcus-strains, as well as against C. albicans

| 293 Kidney epithelial cells | Staphylococcus aureus 325 | Staphylococcus epidermidis RP62A | Candida albicans 5314 |
| --- | --- | --- | --- |
| 42.44 µM | 67 | 67 | 34 |

As can be seen from Table 2, A has an outstanding growth-inhibiting effect against Gram-positive infectious pathogens, such as staphylococci, as well as against yeasts of the species candida albicans, wherein this effect is particularly pronounced against both biofilm-forming staphylococcus-strains. In addition, these strains also exhibit a good therapeutic index. The substance has a lower effect against enterobacteria, such as E. coli, and is fully ineffective against pseudomonades.

5. Inhibition of the Formation of Biofilms by Pathogenic Staphylococci (Exemplary for A and S. epidermidis RP62A)

Use: a) Therapy and prevention of foreign matter-associated infections through biofilm-forming staphylococci in the human and veterinary medicine; b) Prevention of the generation of a staphylococci-biofilm on plastic and metal surfaces Determination of the Formation of Biofilms of Staphylococci on Polystyrene-Surfaces (Biofilm Test)

Technique

For determining the effect of a test compound on the formation of biofilms of staphylococci, the biofilm-reference strain S. epidermidis RP62A is inoculated in trypticase-soy-broth (TSB) with a common 0.25% (w/v) glucose concentration (standard-TSB), and grown over night at 37° C. in a shaking incubator until the stationary growth phase. On the next day, the cultures are diluted 1:100 with fresh TSB, and 100 µl of this germ suspension are pipetted into the wells of a 96-well-polystyrol-tissue culture plate with flat bottom (Greiner, Nürtingen, Germany). In the meantime, also a geometric series of dilutions of the test substance is produced in TSB, and also 100 µl of each of these dilutions are added to the den germ suspensions. The plates were incubated at 37° C. in an incubator for 18 hours at 37° C. On the next day, first the growth of the cultures is checked through determining of the optical density at 550 nm by means of an ELISA-reader (see also at MIC-determination), and documented. Then, the cultures are carefully poured out of the wells, and the plates were washed three times with phosphate-buffered saline solution (PBS), in order to remove non-adherent bacteria. The plates are then dried on a heating block at about 60° C., whereby adherent bacteria are heat-fixed. For dying of the biofilm, then 100 µl of a saturated aqueous crystal violet-solution are pipetted into each of the wells of the plates, that were removed after 5 minutes. Excess dye is subsequently rinsed off under excess running water. After drying, the density of the adherent biofilm is determined with an ELISA-reader at a wavelength of 490 nm.

Results

As can be seen from FIG. 1, A outstandingly inhibits the formation of biofilms of the reference strain S. epidermidis RP62A. At a drug concentration of 0.63 µM, which exactly corresponds to the MIC of the substance in this strain, an about 90% reduction of the formation of bio films compared to a control without the substance can be detected (FIG. 1). This effect decreases in a dose-dependent manner. Interestingly, the biofilm-inhibiting effect is still markedly detectable at those concentrations, which are obviously already too low to influence the growth of the bacteria. Thus, in addition to the above-described growth-inhibiting effect, the substance exhibits an anti-biofilm effect on staphylococci that is independent thereof.

FIG. 1 shows the effect of different concentrations of A on the growth and formation of biofilms of S. epidermidis RP62A.

The invention claimed is:

1. An anti-infective as well as biofilm-inhibiting compound of the general formula 3

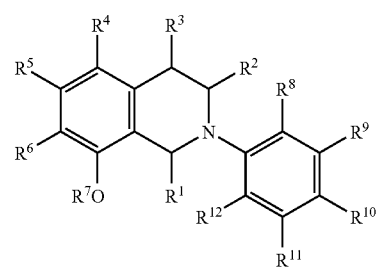

wherein each of $R^1$, and $R^3$ to $R^6$ and $R^8$ to $R^{12}$ independently is H; also $R^1$ to $R^6$ and $R^8$ to $R^{12}$ independently is a non-substituted, monosubstituted or polysubstituted $C_1$-$C_{18}$-alkyl; alkenyl; a non-substituted, monosubstituted or polysubstituted aryl or heteroaryl residue; a non-substituted, monosubstituted or polysubstituted benzyl group; an acyl group; an alkoxy substituent; an alkyl group bound through a sulfur atom; or a nitrogen substituent;

$R^7$ independently can be H; a non-substituted, monosubstituted or polysubstituted $C_1$-$C_{18}$-alkyl, wherein the alkyl can be straight, branched or cyclic; a monosubstituted or polysubstituted, straight, branched or cyclic $C_1$-$C_{18}$-alkenyl; or an acyl group;

and $R^8$ to $R^{12}$ can be bonded in a manner that thereby a non-substituted, monosubstituted or polysubstituted ring and dimers of formula 3 is generated, or a pharmaceutically acceptable salt or solvate of this compound.

2. A composition formulated for the treatment of leishmaniosis diseases, trypanosomal diseases, and/or plasmodial diseases, and or infectious diseases caused by staphylococci, and/or the inhibition of biofilms wherein said composition comprises an anti-infective as well as biofilm-inhibiting compound of the general formulae 1 to 3

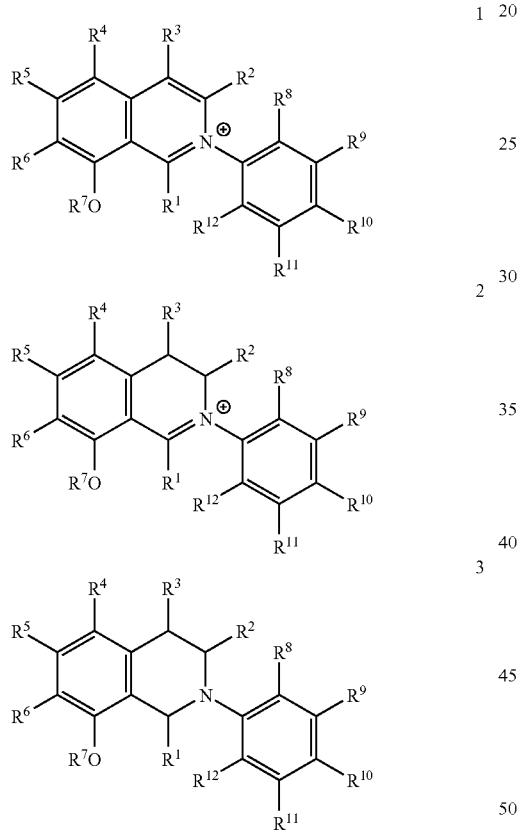

wherein each of $R^1$, and $R^3$ to $R^6$ and $R^8$ to $R^{12}$ independently is H; also $R^1$ to $R^6$ and $R^8$ to $R^{12}$ independently is a non-substituted, monosubstituted or polysubstituted $C_1$-$C_{18}$-alkyl; wherein the alkyl can be straight, branched or cyclic; alkenyl; a non-substituted, monosubstituted or polysubstituted aryl or heteroaryl residue; a non-substituted, monosubstituted or polysubstituted benzyl group; an acyl group; an alkoxy substituent; an alkyl group bound through a sulfur atom; a sulfonyl group; or a nitrogen substituent;

$R^7$ independently can be H; anon-substituted, monosubstituted or polysubstituted $C_1$-$C_{18}$-alkyl, wherein the alkyl can be straight, branched or cyclic; a monosubstituted or polysubstituted, straight, branched or cyclic $C_1$-$C_{18}$-alkenyl; or an acyl group;

and $R^8$ to $R^{12}$ can be bonded in a manner that thereby a non-substituted, monosubstituted or polysubstituted ring and dimers of 1 is generated, or a pharmaceutically acceptable salt or solvate of this compound, with the proviso that formulae 1-3 are not the following formulae and wherein the composition is formulated for the treatment of leishmaniosis diseases, trypanosomal diseases, and/or plasmodial diseases, and/or diseases caused by staphylococci, and the inhibition of biofilms.

3. The compound according to claim 1 of the formula A (=1a)

or a pharmaceutically acceptable salt or solvate of this compound.

4. The compound according to claim 1 of the formula

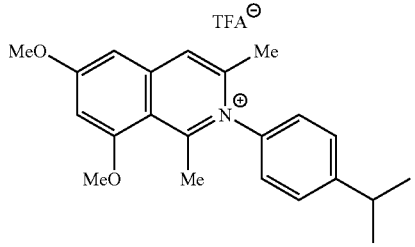

or a biologically active derivative, pharmaceutically acceptable salt, or solvate of this compound.

5. The compound according to claim 1 of the formula

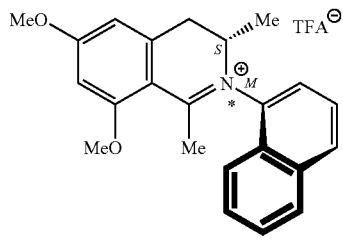

or a biologically active derivative, pharmaceutically acceptable salt, or solvate of this compound.

6. The compound according to claim 1 of the formula

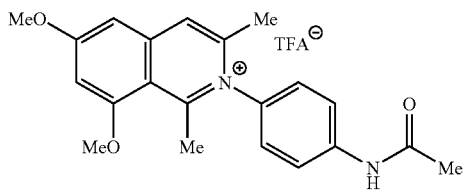

or a biologically active derivative, pharmaceutically acceptable salt, or solvate of this compound.

7. A method for producing a compound according to claim 5, comprising the reaction of 2,6-lutidine, 1-naphthyl boric acid, copper(II)acetate, and myristic acid with a primary amine.

8. A pharmaceutical composition comprising a therapeutically effective amount of a compound according to claim 1, optionally together with suitable additives or excipients.

9. The pharmaceutical composition according to claim 8, characterized in that the compound is present in the form of a depot substance, or as a precursor, together with a suitable pharmaceutically acceptable diluent or carrier substance.

10. The pharmaceutical composition according to claim 8, characterized in that it is present as surface coating, as additive of materials or solutions for rinsing.

11. The pharmaceutical composition according to claim 8 in the form of a tablet; dragée; capsule; drop-solution; suppository; preparation for injection or infusion; or for peroral, rectal or parenteral use.

12. A method for inhibition of biofilms of microorganisms, and/or for the treatment of leishmaniosis diseases, trypanosomal diseases, and/or plasmodial diseases, and/or diseases caused by staphylococci, wherein said method comprises the use of a compound of the general formulae 1 to 3

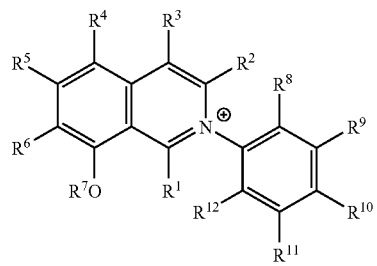

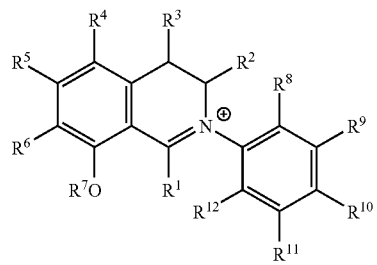

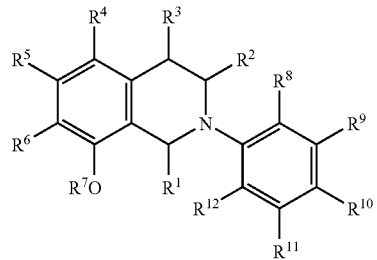

wherein each of $R^1$ to $R^6$ and $R^8$ to $R^{12}$ is independently, either H; a non-substituted, monosubstituted or polysubstituted $C_1$-$C_{18}$-alkyl; wherein the alkyl can be straight, branched or cyclic; alkenyl; a non-substituted, monosubstituted or polysubstituted aryl or heteroaryl residue; a non-substituted, monosubstituted or polysubstituted benzyl group; an acyl group; an alkoxy substituent; an alkyl group bound through a sulfur atom; a sulfonyl group; or a nitrogen substituent;

$R^7$ independently can be either H; a non-substituted, monosubstituted or polysubstituted $C_1$-$C_{18}$-alkyl, wherein the alkyl can be straight, branched or cyclic; a monosubstituted or polysubstituted, straight, branched or cyclic $C_1$-$C_{18}$-alkenyl; or an acyl group;

and $R^8$ to $R^{12}$ can be bonded in a manner that thereby a non-substituted, monosubstituted or polysubstituted ring and dimers of 1 is generated, or a pharmaceutically acceptable salt or solvate of this compound, with the proviso that formulae 1-3 are not the following formulae

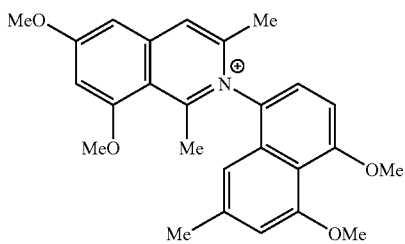

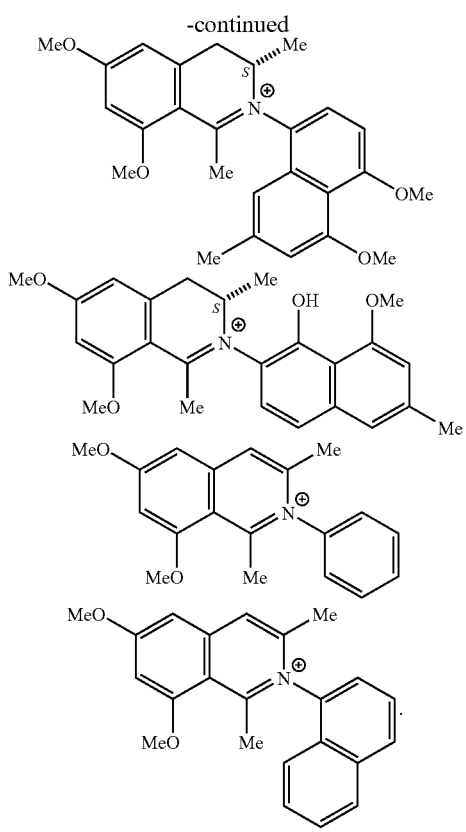

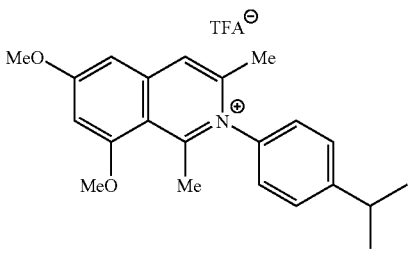

and/or a pharmaceutically acceptable salt or solvate of this compound.

15. The composition, according to claim 2, comprising a compound of the formula:

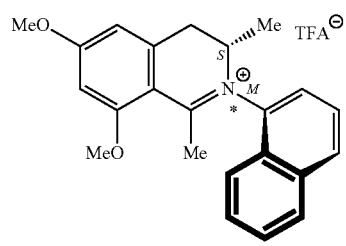

and/or a biologically active derivative, pharmaceutically acceptable salt, or solvate of this compound.

16. The composition, according to claim 2, comprising a compound of the formula:

13. The method according to claim 12 for a treatment of malaria, or the prevention of the formation of biofilms by *S. epidermidis*.

14. The composition, according to claim 2, comprising a compound of the formula A (=1a):

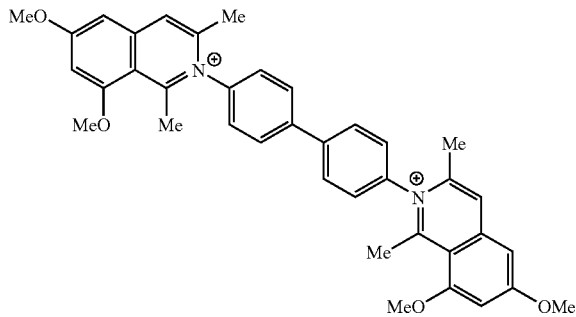

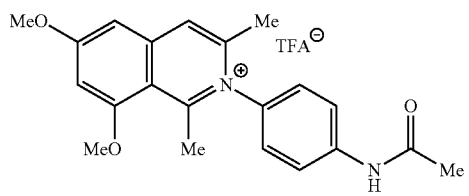

and/or a biologically active derivative, pharmaceutically acceptable salt, or solvate of this compound.

17. The composition, according to claim 2, comprising a compound of the formula:

and/or a biologically active derivative, pharmaceutically acceptable salt, or solvate of this compound.

* * * * *

UNITED STATES PATENT AND TRADEMARK OFFICE
CERTIFICATE OF CORRECTION

PATENT NO. : 8,173,673 B2  
APPLICATION NO. : 12/443318  
DATED : May 8, 2012  
INVENTOR(S) : Gerhard Bringmann et al.

Page 1 of 1

It is certified that error appears in the above-identified patent and that said Letters Patent is hereby corrected as shown below:

Column 2,  
Line 36, "Hellmann" should read --Heilmann--

Column 12,  
Line 34, "[M–CH$_3$]," should read --[M–CH$_3$]$^+$,--

Column 13,  
Line 2, "Mikes," should read --Mikus,--

Signed and Sealed this  
Twenty-fourth Day of July, 2012

David J. Kappos  
*Director of the United States Patent and Trademark Office*